United States Patent

Ikeno et al.

[11] Patent Number: 5,945,466
[45] Date of Patent: Aug. 31, 1999

[54] ROOM TEMPERATURE CURABLE ORGANOPOLYSILOXANE COMPOSITION

[75] Inventors: Masayuki Ikeno, Maebashi; Hideki Sugahara, Gunma-machi, both of Japan

[73] Assignee: Shin-Etsu Chemical Co., Ltd., Tokyo, Japan

[21] Appl. No.: 08/861,219

[22] Filed: May 21, 1997

[30] Foreign Application Priority Data

May 21, 1996 [JP] Japan .................................... 8-149897

[51] Int. Cl.⁶ .................................................. A61K 6/10
[52] U.S. Cl. ........................ 523/109; 524/779; 524/848; 524/451; 524/495
[58] Field of Search ............................. 523/109; 524/779, 524/451, 495, 848

[56] References Cited

U.S. PATENT DOCUMENTS 4,462,936  7/1984  Hechtl et al. ......................... 260/429.7
4,609,678  9/1986  Schwabe et al. ....................... 523/109

*Primary Examiner*—Robert Dawson
*Assistant Examiner*—Caixia Lu-Rutt
*Attorney, Agent, or Firm*—Oblon, Spivak, McClelland, Maier & Neustadt, P.C.

[57] ABSTRACT

A room temperature curable organopolysiloxane composition including:

(A) 100 parts by weight of a diorganopolysiloxane represented by the general formula (1):

$$HO[Si(R^1)_2O]_nH \qquad (1)$$

wherein $R^1$ represents a substituted or unsubstituted monovalent hydrocarbon group, and n is an integer of 15 or more;

(B) from 0.1 part by weight to 20 parts by weight of an organosilane, or a partially hydrolyzed product thereof, represented by the general formula (2):

$$(R^2)_mS(OR^2)_{4-m} \qquad (2)$$

wherein $R^2$'s each independently represent a substituted or unsubstituted monovalent hydrocarbon group, and m is 0, 1 or 2;

(C) from 0.01 part by weight to 10 parts by weight of a curing catalyst;

(D) from 20 parts by weight to 600 parts by weight of a magnesium silicate; and (E) from 5 parts by weight to 80 parts by weight of a paraffin type aliphatic hydrocarbon which is liquid or semi-solid at room temperature. This composition can be rapidly cured, even after a long-term storage.

18 Claims, No Drawings

ROOM TEMPERATURE CURABLE ORGANOPOLYSILOXANE COMPOSITION

BACKGROUND OF THE INVENTION

1. Field of the Invention

This invention relates to a room temperature curable organopolysiloxane composition containing an aliphatic hydrocarbon, and more particularly to a room temperature curable organopolysiloxane composition that can be rapidly cured when used and is especially useful as dental impression materials or impression materials for hand prints, finger prints, external acoustic meatus, ear holes and so forth.

2. Description of the Prior Art

In conventional cases where a room temperature curable organopolysiloxane composition containing a silanol group-containing organopolysiloxane, an alkyl silicate cross-linking agent and a catalyst are used in dental impression materials or impression materials (CA 1015489 and GB 1425607, both corresponding to Japanese Pre-examination Patent Publication (kokai) 48-48753) for hand prints, finger prints, external acoustic meatus, ear holes and so forth, a paraffin type aliphatic hydrocarbon such as liquid paraffin and white vaseline is further added (Japanese Patent Publication (kokoku) 49-7579). This is added so that compositions usually separately stored in two packs can be prevented from adhering to hands when the compositions are mixed and used, and also so that the resulting cured products can be improved in release properties.

However, such a room temperature curable organopolysiloxane composition to which the paraffin type aliphatic hydrocarbon has been added in a necessary quantity has a poor storage stability. More specifically, the paraffin type aliphatic hydrocarbon tends to be oxidized during storage to change into an organic acid, an aldehyde, a hydroperoxide or the like. The organic acid and so forth thus generated causes cure retardation or insufficient curing when the composition is cured. Especially when the human body is compelled to stand still as in the case when dental impression materials are prepared or impressions of external acoustic meatus or ear holes are taken, the composition must be cured in 5 to 10 minutes. A curing time longer than that may cause problems.

SUMMARY OF THE INVENTION

Accordingly, a subject of the present invention is to provide, in the room temperature curable organopolysiloxane composition containing a paraffin type aliphatic hydrocarbon in a stated amount, a composition that can be rapidly cured when used, even after a long-term storage.

The present inventors have discovered that the above subject can be settled when a magnesium silicate is added to the room temperature curable organopolysiloxane composition.

The present invention provides a room temperature curable organopolysiloxane composition comprising;

(A) 100 parts by weight of a diorganopolysiloxane represented by the general formula (1):

$$HO[Si(R^1)_2O]_nH \quad (1)$$

wherein $R^1$ represents a substituted or unsubstituted monovalent hydrocarbon group, and n is an integer of 15 or more;

(B) from 0.1 part by weight to 20 parts by weight of an organosilane, or a partially hydrolyzed product thereof, represented by the general formula (2):

$$(R^2)_m Si(OR^2)_{4-m} \quad (2)$$

wherein $R^2$'s each independently represent a substituted or unsubstituted monovalent hydrocarbon group, and m is 0, 1 or 2;

(C) from 0.01 part by weight to 10 parts by weight of a curing catalyst;

(D) from 20 parts by weight to 600 parts by weight of a magnesium silicate; and (E) from 5 parts by weight to 80 parts by weight of a paraffin type aliphatic hydrocarbon which is liquid or semi-solid at room temperature.

The room temperature curable organopolysiloxane composition of the present invention may cause neither cure retardation nor faulty curing when used, even after a long-term storage. Hence, it is especially useful as dental impression materials or impression materials for hand prints, finger prints, external acoustic meatus, ear holes and so forth.

DETAILED DESCRIPTION OF THE PREFERRED EMBODIMENTS

The present invention will be described below in detail.

The room temperature curable organopolysiloxane composition of the present invention basically contains a component-(A) specific diorganopolysiloxane, a component-(B) specific organosilane, a component-(C) curing catalyst, a component-(D) magnesium silicate and a component-(E) paraffin type aliphatic hydrocarbon.

Component (A)

The component (A) of the present invention is a straight-chain diorganopolysiloxane blocked with silanol groups at the both terminals of its molecular chain, represented by the general formula (1):

$$HO[Si(R^1)_2O]_nH \quad (1)$$

wherein $R^1$ represents a substituted or unsubstituted monovalent hydrocarbon group, and n is an integer of 15 or more.

In the general formula (1), the substituted or unsubstituted monovalent hydrocarbon group represented by $R^1$ may include those having 1 to 12 carbon atoms, preferably excluding aliphatic unsaturated bonds, and more preferably those having 1 to 8 carbon atoms. It may include, e.g., alkyl groups such as a methyl group, an ethyl group, a propyl group, a butyl group, a hexyl group, an octyl group and a decyl group; cycloalkyl groups such as a cyclopentyl group, a cyclohexyl group and a cycloheptyl group; alkenyl groups such as a vinyl group, an allyl group, a propenyl group, an isopropenyl group, a butenyl group, an isobutenyl group, a hexenyl group and a cyclohexenyl group; aryl groups such as a phenyl group and a tolyl group; aralkyl groups such as a benzyl group and a phenylethyl group; and any of these at least one or all the hydrogen atoms of the organic group of which has or have been substituted with a halogen atom(s) or a cyano group(s), as exemplified by a chloromethyl group, a trifluoropropyl group and a cyanoethyl group. A methyl group, a phenyl group and a trifluoropropyl group are preferred.

Letter symbol n in the general formula (1) represents an integer of 15 or more, typically an integer of from 15 to 2,000, and preferably an integer of from 50 to 900, more preferably from 100 to 500. If the value of n is smaller than 15, the resulting cured product may have a poor mechanical strength. The viscosity depends also on the value of n, and the compound may have a viscosity at 25° C. of from 25 cP or above, and preferably in the range of from 700 to 1,000,000 cP.

The diorganopolysiloxane represented by the general formula (1) can be synthesized by conventional known methods.

Component (B)

The component (B) of the present invention is an organosilane, or a partially hydrolyzed product thereof, represented by the general formula (2):

$$(R^2)_m Si(OR^2)_{4-m} \qquad (2)$$

wherein $R^2$'s each independently represent a substituted or unsubstituted monovalent hydrocarbon group, and m is 0, 1 or 2. This component has the function to cause the composition to cure at room temperature (for example, at 0 to 40° C., typically at 5 to 35° C.) in the presence of water in the atmosphere.

In the compound of the general formula (2), the substituted or unsubstituted monovalent hydrocarbon group represented by $R^2$ may include the same groups as those exemplified as $R^1$ in the general formula (1) and also alkoxyl substituted alkyl groups such as a methoxyethyl group and an ethoexyethyl group.

The component (B) may include, e.g., tetraalkoxysilanes such as tetramethoxysilane, tetraethoxysilane, tetra(methoxyethoxy)silane, tetrapropoxysilane and tetrapbutoxysilane; organotrialkoxysilanes such as methyltrimethoxysilane, methyltriethoxysilane, vinyltrimethoxysilane, vinyltriethoxysilane, phenyltrimethoxysilane, phenyltriethoxysilane, 3-chloropropyltrimethoxysilane, chloropropyltriethoxysilane and 3-aminopropyltriethoxysilane; organosilicates such as ethyl orthosilicate and propyl orthosilicate; and partially hydrolyzed products of these. Methyltrimethoxysilane, tetraethoxysilane and ethylorthosilicate are preferred.

Any of these may be used alone or in combination of two or more.

The component (B) may be mixed in an amount of from 0.1 to 20 parts by weight, and preferably from 0.5 to 8 parts by weight, based on 100 parts by weight of the component (A). If the component (B) is too less than 0.1 part by weight, no sufficient cross-linking may proceed. If on the other hand it is more than 20 parts by weight, the resulting cured product may be brittle, resulting in a decrease in mechanical strength.

Component (C)

As the component-(C) curing catalyst, known catalysts conventionally used in compositions of this type may be used. The component (C) typically includes an organic metal compound containing, for example, tin, titanium, zirconium, iron, lead, zinc, cobalt, manganese or aluminum as a metallic element. Specifically, the component (C) is exemplified by tin carboxylates such as tin octenoate, tin naphthenate, stannous caprylate and tin oleate; tin compounds such as dibutyltin diacetate, dibutyltin dioctoate, dibutyltin dilaurate, dibutyltindioleate, diphenyltin diacetate, dibutyltin oxide, dibutyltin dimethoxide, dibutylbis(triethoxysiloxy)tin, dibutyltin benzylmaleate, dioctyltin dilaurate, dioctyltin dioctoate and dioctyltin dilaurate; metal alkoxides such as tetramethyl titanate, tetraethyl titanate, tetrapropyl titanate, tetrabutyl titanate and tetraethoxyzirconate; and organic metal compounds such as iron octenoate, iron naphenate, lead naphenate, zinc naphenate, zinc stearate, zinc-2-ethylhexoate, lead-2-ethyloctoate, iron-2-ethylhexoate, cobalt-2-ethylhexoate, manganese-2-ethylhexoate, cobalt naphthenate and alkoxyaluminum compounds. In particular, dibutyltin dilaurate and dioctyltin dilaurate are preferred.

The component-(C) curing catalyst may be mixed in an amount of from 0.01 to 10 parts by weight, and preferably from 0.01 to 5 parts by weight, based on 100 parts by weight of the component (A). If the component (C) is less than 0.01 part by weight, no sufficient catalytic function may be exhibited. If on the other hand it is more than 10 parts by weight, the resulting cured product may have a poor thermal resistance.

Component (D)

The component (D) of the present invention is a magnesium silicate, and preferably magnesium tetrasilicate represented by the formula:

$$3MgO.4SiO_2.H_2O$$

or hydrous magnesium silicate such as talc.

The magnesium silicate acts as a filler in the composition of the present invention. This magnesium silicate also has the function to prevent the cure retardation or insufficient curing when the composition of the present invention is used, because it absorbs the organic acid, aldehyde, hydroperoxide and so forth produced as a result of the oxidation of the component-(E) paraffin type aliphatic hydrocarbon during storage.

The magnesium silicate may usually have an average particle diameter of from 0.1 to 50 μm, and preferably from 1 to 20 μm. The average particle diameter can be measured as a weight average value by analyzing methods such as laser diffractometry. If it has a too small average particle diameter, the composition may have a great kneading resistance to cause a poor workability. If on the other hand it has a too large average particle diameter, the resulting cured product may have a poor surface uniformity.

The magnesium silicate may be mixed in an amount of from 20 to 600 parts by weight, preferably from 40 to 400 parts by weight, and particularly from 100 to 300 parts by weight, based on 100 parts by weight of the component (A). If the amount is less than 20 parts by weight, an insufficient storage stability may result and also no sufficient hardness can be imparted to the resulting cured product. If on the other hand the amount is more than 600 parts by weight, the composition may have a great kneading resistance to cause a poor workability. Also, the resulting cured product may have a high hardness.

Component (E)

The component (E) in the present invention is a paraffin type aliphatic hydrocarbon (i.e., methane family hydrocarbons having essentially no aliphatic unsaturation) which is liquid or semi-solid or can change the shape with its weight when left to stand at room temperature (for example, 0 to 40° C., typically 5 to 35° C.) and is not compatible with the component (A). It may preferably be a paraffin type aliphatic hydrocarbon having 25 to 350 carbon atoms and containing almost no lower hydrocarbon having not more than 18 carbon atoms, and may more preferably be liquid paraffin and white vaseline.

The component (E) makes it easy to mix and knead compositions comprised of two packs and improves release properties of the resulting cured product.

The component (E) may be mixed in an amount of from 5 to 80 parts by weight, and preferably from 15 to 60 parts by weight, based on 100 parts by weight of the component (A). If the component (E) is less than 5 parts by weight, no sufficient release properties can be obtained. If on the other hand it is more than 80 parts by weight, the component (E) may exude from the resulting cured product.

Other Additives

In the room temperature curable organopolysiloxane composition of the present invention, in addition to the components (A) to (D), other additives may be optionally used. For example, such additives may include reinforcing fillers such as fumed silica and precipitated silica; non-reinforcing fillers such as quartz powder, diatomaceous earth and calcium carbonate; heat-resistance improvers such as tin oxide, aluminum oxide, carbon black and red iron oxide; colorants; and thixotropy-providing agents such as polyether. Any of these additives may be used alone, or in combination of two or more.

These additives may be mixed in any desired amount appropriately determined within the range that does not damage the object of the present invention.

The composition of this invention can be used as a impression material for molding the shape inside the hole of an ear. Thus, the present invention provides a method of molding the shape inside the hole of an ear, which comprises charging the composition according to the present invention into said hole and curing the composition therein to form the impression of said hole, and taking the cured molded product out of the hole.

The composition of this invention can be also used a dental impression material for preparing the impression of a tooth. Thus, the present invention provides a method of preparing the impression of a tooth or teeth, which comprises applying the composition according to the present invention on a tooth or teeth, curing the composition and taking the resulting cured product with the impression of the tooth or teeth therefrom.

EXAMPLES

The present invention will be described below in greater detail by giving Examples and Comparative Examples. In the following Examples and Comparative Examples, viscosity is indicated as a value measured at 25° C.

EXAMPLE 1

Using a mixing stirrer, 50 parts by weight of dimethylpolysiloxane blocked with silanol groups at the both terminals of its molecular chain and having a viscosity of 20,000 cP, 50 parts by weight of dimethylpolysiloxane raw rubber blocked with trimethylsilyl groups at the both terminals of its molecular chain and having an average degree of polymerization of 8,000, 220 parts by weight of magnesium tetrasilicate having an average particle diameter of 5 μm and 20 parts by weight of liquid paraffin (density: 0.88 g/cm$^3$; viscosity: 140 cSt) were mixed at 25° C. to obtain a pasty mixture.

Subsequently, to 100 parts by weight of the pasty mixture thus obtained, 1.4 parts by weight of tetraethoxysilane and 1 part by weight of dibutyltin dilaurate were added at 25° C., followed by kneading, where the time taken until the composition cured and the hardness thereof at 30 minutes after the kneading was started were measured. The hardness was measured using a type-A spring tester according to JIS-K6301.

Results obtained are shown in Table 1.

EXAMPLE 2

A room temperature curable organopolysiloxane composition was prepared and cured in the same manner as in Example 1 except that the pasty mixture obtained therein was further left to stand at a temperature of 80° C. for 7 days to undergo accelerated deterioration when used. The time until it cured and the hardness after 30 minutes were also measured.

Results obtained are shown in Table 1.

COMPARATIVE EXAMPLE 1

A room temperature curable organopolysiloxane composition was prepared and cured in the same manner as in Example 1 except that the magnesium tetrasilicate used therein was replaced with quartz powder having an average particle diameter of 4 μm. The time until it cured and the hardness after 30 minutes were also measured.

Results obtained are shown in Table 1.

COMPARATIVE EXAMPLE 2

A room temperature curable organopolysiloxane composition was prepared and cured in the same manner as in Comparative Example 1 except that the pasty mixture obtained therein was further left to stand at a temperature of 80° C. for 7 days to undergo accelerated deterioration when used. The time until it cured and the hardness after 30 minutes were also measured.

Results obtained are shown in Table 1.

EXAMPLE 3

Using a mixing stirrer, 74 parts by weight of dimethylpolysiloxane blocked with silanol groups at the both terminals of its molecular chain and having a viscosity of 100,000 cP, 26 parts by weight of dimethylpolysiloxane blocked with silanol groups at the both terminals of its molecular chain and having a viscosity of 700 cP, 50 parts by weight of magnesium tetrasilicate having an average particle diameter of 5 μm and 33 parts by weight of liquid paraffin (density: 0.88 g/cm³; viscosity: 140 cSt) were mixed at 25° C., followed by heating at a temperature of 120° C. for 1 hour to obtain a pasty mixture.

Next, 100 parts by weight of the pasty mixture thus obtained, 1.4 parts by weight of tetraethoxysilane and 1 part by weight of dibutyltin laurate were kneaded at 25° C., where the time taken until the composition cured and the hardness thereof at 30 minutes after the kneading was started were measured. Results are given in Table 1.

TABLE 1

|  | Curing time (min.) | Hardness |
|---|---|---|
| Example 1 | 10 | 42 |
| Example 2 | 10 | 41 |
| Example 3 | 6 | 19 |
| Comparative Example 1 | 13 | 40 |
| Comparative Example 2 | 20 | 40 |

EXAMPLE 4

The composition prepared in Example 3 was left to stand at a temperature of 80° C. for 7 days to undergo accelerated deterioration. The time required until it cured and the hardness 30 minutes after it had cured were also measured. The time was measured as 6 minutes, and the hardness was measured as 19.

COMPARATIVE EXAMPLE 3

A room temperature curable organopolysiloxane composition was prepared and cured in the same manner as in Example 3 except that the magnesium tetrasilicate used therein was replaced with a mixture of 110 parts by weight of quartz powder having an average particle diameter of 4 μm and 110 parts by weight of calcium carbonate having an average particle diameter of 1.5 μm. The time required until it cured and the hardness 30 minutes after it had cured were also measured. The time was measured as 15 minutes, and the hardness was measured as 35.

COMPARATIVE EXAMPLE 4

The composition prepared in comparative Example 3 was left to stand at a temperature of 80° C. for 7 days to undergo accelerated deterioration. The time required until it cured and the hardness 30 minutes after it had cured were also measured. The time was measured as 30 minutes, and the hardness was measured as 20.

What is claimed is:

1. A room temperature curable organopolysiloxane composition comprising;
    (A) 100 parts by weight of a diorganopolysiloxane represented by the general formula (1):

$$HO[Si(R^1)_2O]_mH \qquad (1)$$

wherein $R^1$ represents a substituted or unsubstituted monovalent hydrocarbon group, and n is an integer of 15 or more;

(B) from 0.1 part by weight to 20 parts by weight of an organosilane, or a partially hydrolyzed product thereof, represented by the general formula (2):

$$(R^2)_m Si(OR^2)_{4-m} \qquad (2)$$

wherein $R^2$'s each independently represent a substituted or unsubstituted monovalent hydrocarbon group, and m is 0, 1 or 2;

(C) from 0.01 part by weight to 10 parts by weight of a curing catalyst;
    (D) from 20 parts by weight to 600 parts by weight of a magnesium silicate; and
    (E) from 5 parts by weight to 80 parts by weight of a paraffin type aliphatic hydrocarbon which is liquid or semi-solid at room temperature.

2. The composition of claim 1, wherein in the general formula (1) representing the component (A), the $R^1$ each represent unsubstituted or substituted hydrocarbon groups having 1 to 12 carbon atoms but having no aliphatic unsaturated bonds.

3. The composition of claim 1, wherein the $R^1$ each represents alkyl groups, cycloalkyl groups, alkenyl groups, aryl groups, aralkyl groups, or corresponding substituted groups in which at least one of the hydrogen atoms possessed by these hydrocarbon groups has been substituted by a halogen atom(s) or a cyano group(s).

4. The composition of claim 1, wherein the $R^1$ is each a methyl group, a phenyl group or trifluoropropyl group.

5. The composition of claim 1, wherein n in the general formula (1) represents an integer of 15 to 2,000.

6. The composition of claim 1, wherein in the general formula (2) $R^2$ each represent unsubstituted or substituted hydrocarbon groups having 1 to 12 carbon atoms but having no aliphatic unsaturated bonds.

7. The composition of claim 1, wherein the organosilane of the component (B) is a tetraalkoxysilane, an organotrialkoxysilane, an alkylsilicate, a partially hydrolyzed product of these, or a mixture of two or more of the compounds.

8. The composition of claim 1, wherein the organosilane of the component (B) is present in an amount of from 0.1 to 20 parts by weight per 100 parts by weight of the component (A).

9. The composition of claim 1, wherein the curing catalyst of the component (C) is an organic metal compound containing tin, titanium, zirconium, iron, lead, zinc, cobalt, manganese or aluminum as a metallic element.

10. The composition of claim 9, wherein the curing catalyst is selected from dibutyltin dilaurate or dioctyltin dilaurate.

11. The composition of claim 1, wherein the component (C) curing catalyst is present in an amount of from 0.01 to 10 parts by weight per 100 parts by weight of the component (A).

12. The composition of claim 1, wherein the component (D) is magnesium tetrasilicate or hydrous magnesium silicate.

13. The composition of claim 1, wherein the magnesium silicate has an average particle diameter of from 0.1 to 50 µm.

14. The composition of claim 1, wherein the magnesium silicate of the component (D) is present in an amount of from 20 to 600 parts by weight per 100 parts by weight of the component (A).

15. The composition of claim 1, wherein the paraffin aliphatic hydrocarbon of the component (E) has 25 to 350 carbon atoms and containing substantially no lower hydrocarbon having not more than 18 carbon atoms.

16. The composition of claim 1, wherein the component (E) is present in an amount of from 5 to 80 parts by weight per 100 parts by weight of the component (A).

17. A impression material for molding the shape inside the hole of an ear, comprised of the composition as defined in claim 1.

18. A dental impression material for preparing the impression of a tooth or teeth, comprised of the composition as defined in claim 1.

* * * * *